United States Patent [19]

Sato et al.

[11] 4,282,005

[45] Aug. 4, 1981

[54] BODY WARMER FOR HEATING BY EXOTHERMIC HEAT

[75] Inventors: Masaharu Sato; Michio Sugiura, both of Tokyo, Japan

[73] Assignee: Kensen Co., Ltd., Tokyo, Japan

[21] Appl. No.: 106,742

[22] Filed: Dec. 26, 1979

[30] Foreign Application Priority Data

Mar. 5, 1979 [JP] Japan ............... 54-27763[U]

[51] Int. Cl.$^3$ ............... F24J 1/00; A61F 7/00
[52] U.S. Cl. ............... 44/3 R; 44/3 C; 126/204; 126/206
[58] Field of Search ............... 44/3 R, 3 C; 126/204, 126/206, 263

[56] References Cited

U.S. PATENT DOCUMENTS

| | | | |
|---|---|---|---|
| 2,250,009 | 7/1941 | Coble | 44/3 R |
| 3,547,100 | 12/1970 | Usui | 126/206 |
| 4,093,424 | 6/1978 | Yoshida et al. | 44/3 C |
| 4,114,591 | 9/1978 | Nakagawa | 126/263 |

*Primary Examiner*—Carl F. Dees
*Attorney, Agent, or Firm*—George B. Oujevolk

[57] ABSTRACT

A body warmer for heating a human body by means of exothermic heat which consists of a particulate exothermic substance containing a main constituent for reducing a metallic oxide with the air and water content externally supplied for heating the body by the chemical reaction thereof, a fibrous agricultural solid waste impregnated with sodium chloride, bitter or composition salt, and an air permeable bag for filling the exothermic substance and the fibrous agricultural solid waste. Thus, the body warmer can heat at safe and effective temperature continuously for extremely long time so as to cure even neuralgia.

1 Claim, 1 Drawing Figure

U.S. Patent  Aug. 4, 1981  4,282,005
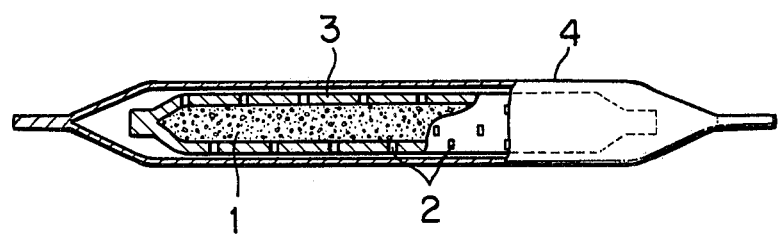

BODY WARMER FOR HEATING BY EXOTHERMIC HEAT

BACKGROUND OF THE INVENTION

This invention relates to a body warmer for heating a human body having a chilly constitution and, more particularly, to a body warmer for heating by utilizing an exothermic heat generated by means of the oxidation and reduction reaction of metallic oxide or the like.

A body warmer has a wide range of applications for the purposes of not only curing a neuralgia, rheumatism, etc. but heating a human body having a chilly constitution or working outside in winter. There has recently been proposed a body warmer which utilizes exothermic heat using a metallic oxide or the like conveniently usable instead of gas oil or a ball briquette. The conventional body warmer utilizing an exothermic heat has the disadvantage of excessively high exothermic temperature. It has been accepted to preferably heat the human body at approx. 52° to 55° C. for the purpose of therapy and heating. However, the conventional body warmer disadvantageously heats at a higher temperature than this preferable temperature and sometimes heats at higher than 70° to 80° C. resulting in danger to the body. The conventional body warmer has another disadvantage of very short lasting exothermic duration such as approx. 5 to 6 hours at an appropriate temperature in the case of exothermic heat. It is accordingly necessary to replace the body warmer several times with a result of inconvenience and lack of economy. A conventional body warmer has mixed a copper dioxide so as to lengthen the lasting exothermic duration. However, the copper is toxic and introduces a danger of adverse effect to the human body.

SUMMARY OF THE INVENTION

The inventors of the present invention contemplate to eliminate the aforementioned disadvantages of the conventional body warmer for heating by utilizing exothermic heat by repeated studies and have discovered that they are able to overcome all the disadvantages of the conventional body warmer by mixing a fibrous agricultural solid waste impregnated with sodium chloride such as common salt or a composition salt or the like so as to thus complete the present invention.

It is, therefore, an object of the present invention to provide a body warmer for heating a human body by means of exothermic heat which can heat at a safe and effective temperature to be usable for aged and young people withou anxiety.

Another object of the present invention is to provide a body warmer for heating a human body by means of exothermic heat which can continuously heat for an extremely long time to eliminate troublesome exchanges frequently.

Yet another object of the present invention is to provide a body warmer for heating a human body by means of exothermic heat which has no danger of pollution.

Still another object of the present invention is to provide a body warmer for heating a human body by means of exothermic heat which can effectively cure a neuralgia, smooth a human skin, and soften human muscle.

In a preferred aspect of this invention, there is provided a body warmer for heating a human body by means of exothermic heat which comprises a particulate exothermic substance containing a main constituent for reducing a metallic oxide with air and water content externally supplied for heating by means of a chemical reaction, a fibrous agricultural solid waste impregnated with sodium chloride, bitter or composition salt, and an air permeable bag for filling the particulate exothermic substance and fibrous agricultural solid waste.

BRIEF DESCRIPTION OF THE DRAWING

The above and other related objects and features of the invention will be apparent from the following description of the disclosure and the accompanying drawings and the novelty thereof pointed out in the appended claims.

The sole FIGURE is a partially fragmentarily front view of one preferred embodiment of the body warmer constructed according to the present invention.

DETAILED DESCRIPTION OF THE PREFERRED EMBODIMENTS

The invention will be described in more detail hereinafter with reference to the specific example of the body warmer described and exemplified in the accompanying drawing.

The particulate exothermic substance used in the body warmer includes, for example, a metallic oxide such as a ferrosoferric oxide, manganese dioxide, etc., a carbon, iron filings or dusts, etc. as main constituents in a predetermined ratio of combination thereof. It is known that such a particulate exothermic substance is heated by means of chemical reaction upon absorption of air and water content externally through the air permeable bag.

The advantageous feature of the present invention resides in a mixture of the above described exothermic substance with a fibrous agricultural solid waste impregnated with sodium chloride, bitter or composition salt. The fibrous agricultura solid waste thus mixed includes, for example, a residual substance or substances extracted or squeezed from an agricultural plant with essential agricultural product or products and formed in fibrous such as beet waste extracted from a beet with sugar, a bagasse squeezed from a sugar cane with sugar sap, or straws, etc.

The fibrous agricultural solid waste thus obtained is then dipped in a sodium chloride such as common salt, a bitter or a composition salt dissolved in an aqueous solution, preferably contained in approx. 10 weight percent to absorb the solution and to be used as it is or as it is removed with excessive water content therefrom as required.

The fibrous agricultural solid waste restricts abrupt exothermic reaction and further incorporates its heat storage of regeneration. The sodium chloride impregnated in the fibrous agricultural solid waste is operated to absorb externally water content and to gradually supply the water content absorbed through the fibrous agricultural solid waste to the reaction system. Therefore, the body warmer of this invention thus consisting of a fibrous agricultural solid waste impregnated with the sodium chloride or the like can continuously provide heat at an appropriate temperature for extremely long time.

A bag for filling the aforementioned particulate exothermic substance and the fibrous agricultural solid waste must incorporate an air permeability so as to absorb necessary air and water content externally. The bag is formed, for example, of Japanese paper, a non-woven fabric or the like, or Japanese paper, non-woven fabric or woven or knitted cloth partially or entirely laminated on the back surface thereof with a resin film or the like and perforated with fine pores.

Preferred example of a content to be filled in the bag comprises by weight percent:
  20% of ferrosoferric oxide,
  25% of manganese dioxide,
  5% of magnesium oxide,
  2% of holmium oxide,
  4% of sodium chloride,
  2-15%, preferably 5% of beet failings or lees,
  1% of boron oxide,
  3% of pearlite,
  5% of carbon, and
  40% of iron filings or dusts, The boron oxide of the above content is operated to gradually solidify the particulate exothermic substance as the exothermic reaction proceeds, and further to react with alkali exhausted from human skin to smooth the skin.

Preferred example of the content may also comprise in mixture a methyl salicylate so as to soften human muscle by penetrating into the skin upon exothermic reaction of the particulate exothermic substance.

Referring now to the drawing showing one preferred embodiment of the body warmer constructed according to the present invention, the body warmer contains a content 1 consisting of a particulate exothermic substance including a metallic oxide, carbon, etc., and a fibrous agricultural solid waste impregnated with sodium chloride or the like, and a bag 3 incorporating fine pores 2 for filling the content 1. It is noted that the metallic oxide is not preferably mixed with other components when filling the contents in the bag 3. The bag 3 thus filled with the content 1 is further sealed in vacuum by a sheathed bag 4 which is composed of high molecular film or the like and not permeable with fluid or air. Since the body warmer thus sealed with the sheathed bag 4 is isolated externally from the air and water, it does not heat by the exothermic reaction and can be preserved for a long time.

When this body warmer is used, the sheathed bag 4 is broken, and the inner body warmer thus exposed is vibrated as required to sufficiently mix the contents filled in the bag 3 and is then retained in contact with the human skin to thus gradually heat the human body.

It should be understood from the foregoing description that since the body warmer of this invention is thus constructed and operated, it can heat at a safe and effective temperature. Although the conventional body warmer heats exceedently at approx. 70° to 80° C. to thus adversely affect the internal organs of the human body and to even introduce a danger of scalding on the skin, the body warmer of this invention is effective for curing, since maintaining at approx. 52° to 55° C., neuralgia to be usable for aged and young people without anxiety. It should also be appreciated that the body warmer of this invention can heat the body for an extremely long time while the conventional body warmer can only heat for approx. 5 to 6 hours of lasting exothermic duration, the body warmer of this invention can continuously heat even over approximately 24 hours to thereby eliminate troublesome replacement thereof frequently but to conduct only once per day conveniently and economically. It should also be appreciated that since the body warmer of this invention employs no copper dioxide nore toxic substance even as the contents and bags against human body and skin, there is no danger of pollution. It should also be understood that since the body warmer of this invention can continuously heat at an appropriate temperature for a long time, it can effectively cure a neuralgia or the like, can smooth a human skin because the boron oxide smooths the body skin, and can soften human muscle because methyl salicylate can soften the human muscle. It should further be appreciated that since the body warmer of this invention is easy to handle, it is very useful for the health treatment of aged and young people.

What is claimed is:

1. A body warmer for heating a human body by exothermic heat comprising:
   (a) an elongated air permeable paper bag for holding heat producing materials
   (b) a sheath bag disposed around said air permeable bag; and,
   (c) heat producing materials in said paper bag consisting of
      about 20 parts of ferrosoferric oxide
      about 25 parts of manganese dioxide
      about 5 parts of magnesium oxide
      about 2 parts of holmium oxide
      about 4 parts of sodium chloride
      about 2 to 15 parts of sugar-beat waste materials
      about 1 part boron oxide
      about 3 parts of pearlite
      about 5 parts of carbon, and
      about 40 parts of iron filings or iron dust.

* * * * *